United States Patent [19]
Inaba et al.

[11] Patent Number: 5,403,279
[45] Date of Patent: Apr. 4, 1995

[54] BLOOD COLLECTING APPARATUS

[75] Inventors: Fumiaki Inaba; Satoshi Inoue, both of Fujinomiya, Japan

[73] Assignee: Terumo Kabushiki Kaisha, Tokyo, Japan

[21] Appl. No.: 240,493

[22] Filed: May 10, 1994

Related U.S. Application Data

[63] Continuation of Ser. No. 947,097, Sep. 17, 1992, abandoned, which is a continuation of Ser. No. 623,669, Dec. 26, 1990, abandoned.

[30] Foreign Application Priority Data

Jun. 29, 1988 [JP] Japan ................. 63-159404
Jun. 29, 1988 [JP] Japan ................. 63-159405

[51] Int. Cl.$^6$ ..................... A61M 1/02; A61B 5/14
[52] U.S. Cl. ..................... 604/65; 604/245; 604/403; 128/771
[58] Field of Search ............ 604/4, 65, 67, 245, 604/403, 903; 128/770, 771

[56] References Cited

U.S. PATENT DOCUMENTS

| | | | |
|---|---|---|---|
| 2,982,286 | 5/1961 | Welch, Jr. | 604/245 |
| 3,657,926 | 4/1972 | Munson et al. | 73/717 |
| 3,689,748 | 9/1972 | Bothne | 73/4 R |
| 3,790,910 | 2/1974 | McCormack | 73/4 R |
| 4,375,838 | 3/1983 | Yano et al. | |
| 4,402,373 | 9/1983 | Comeau | 128/771 |
| 4,532,809 | 8/1985 | Antonazzi et al. | 73/718 |
| 4,606,420 | 8/1986 | Silver | 128/771 |
| 4,667,153 | 5/1987 | Doyle. | |
| 4,672,974 | 6/1987 | Lee. | |
| 4,712,567 | 12/1987 | Gille et al. | 128/771 |
| 4,922,922 | 5/1990 | Pollock et al. | 128/771 |
| 4,923,449 | 5/1990 | Toya et al. | |

FOREIGN PATENT DOCUMENTS

| | | |
|---|---|---|
| 0044707 | 1/1982 | European Pat. Off. . |
| 2353840 | 12/1977 | France . |
| 2606639 | 5/1988 | France . |
| 51-3153 | 1/1976 | Japan . |
| 63-23644 | 1/1988 | Japan . |
| 1537596 | 1/1979 | United Kingdom . |

*Primary Examiner*—Ralph A. Lewis
*Attorney, Agent, or Firm*—Frishauf, Holtz, Goodman & Woodward

[57] ABSTRACT

A blood collecting apparatus includes a measuring device provided with a sensor for measuring the amount of collected blood when blood is collected into a blood container, and a controller for calculating the amount of collected blood based on an output y of the measuring sensor. The output y is a function of an n-times measured weight w of collected blood such that $y = aw + b$, wherein a and b are constants characteristic of the measuring sensor. The controller detects the output $y_i$ of the measuring sensor in $n+1$ units of respective known amounts $w_i$ of collected blood, and corrects the constants a and b on the basis of such detected data. The controller, moreover, automatically detects the output $y_0$ of the measuring sensor every predetermined cycle in a state where the measured weight w of collected blood is zero, and corrects the constant b of the function $y = aw + b$ on the basis of such detected output $y_0$.

4 Claims, 8 Drawing Sheets

BLOOD COLLECTING APPARATUS

This application is a Continuation of application Ser. No. 07/947,097, filed Sep. 17, 1992, (abandoned) which is a Continuation of application Ser. No. 07/623,669, filed Dec. 26, 1990, (abandoned).

This invention relates to a blood collecting apparatus for collecting blood into a blood container.

BACKGROUND OF THE INVENTION

Heretofore, there was proposed a blood collecting apparatus as described in Japanese patent publication No. Sho 51-3153.

A blood collecting apparatus, in general, must include a sensor for measuring the amount of blood collected into a blood container.

In a blood collecting apparatus for collecting blood into a blood container by negative pressure to be generated by a vacuum pump, the blood collecting apparatus must be provided with a pressure sensor for measuring pressure in a blood collecting evacuated chamber where the blood container is to be set.

(I) The measuring sensor and pressure sensor can be handled such that the output of those sensors is in a certain relationship with the measured weight (amount of collected blood or pressure), which can be expressed as a constant function. Therefore, a blood collecting apparatus is provided with control means for calculating a desired measured weight (amount of collected blood or pressure) on the assumption that the output of the measuring sensor can be expressed as the above-mentioned specific function.

Taking the sensor for measuring the amount of collected blood as representing the other, if it is handled such that the output y of the measuring sensor is in a certain relation with the measured weight w of collected blood, which can be expressed as the linear function $y = aw + b$ (wherein a: gain [sensitivity] and b: offset value), the constants a and b are characteristics inherent to the individual sensors are thus different for each sensor from the beginning.

Therefore, in a blood collecting apparatus using a sensor as stated above, it is required that the constants are properly changed for correction in the early stage of the use of such sensor and also in the transit stage of the use thereof, so that the amount of collected blood calculated by control means based on the output of the sensor always coincides with a proper value.

At that time, it can be considered that the correction of changing the constants a and b of the sensors is effected by providing a change circuit and that the output signals of the sensor are adjusted by volume or the like. However, this idea has, for example, the following inconveniences. ① a conversion circuit is required and ② the volume, etc. must be adjusted in the manufacturing process and in the using process.

An object of the present invention is to correct the characteristics of a sensor for measuring the amount of collected blood with ease and to obtain accuracy in measurement of the amount of collected blood.

Another object of the invention is to correct the characteristics of a pressure sensor and to obtain accuracy in measurement of pressure generated in a blood collecting evacuated chamber.

(II) Similarly, taking the sensor for measuring the amount of collected blood as representing the other sensor, if it is handled such that the output y of the measuring sensor is in a certain relationship with the measured weight w of collected blood, which can be expressed as the linear function $y = aw + b$ (wherein a: gain [sensitivity] and b: offset value), the offset value b sometimes drifts with the passage of time because of heat and changes in stress, as is generally characteristic of sensors (see FIG. 8).

Accordingly, when the offset value $b_{01}$ of the linear function initialized in the control means should be drifted in such a way as $b_{02}, b_{03} \ldots$ during the use, error values $(b_{02}-b_{01}), (b_{03}-b_{01})\ldots$ would occur unless they are corrected.

A further object of the present invention is to normally and automatically correct the change of the offset value of the output of a sensor for measuring the amount of collected blood caused by drift and to obtain accuracy in measurement of the amount of collected blood.

A still further object of the present invention is to normally and automatically correct the change of the offset value of the output of a pressure sensor for measuring the amount of collected blood caused by drift and also to obtain accuracy in measurement of the pressure formed in blood collecting evacuated chamber.

SUMMARY OF THE INVENTION

A blood collecting apparatus, comprises a blood collecting chamber; a blood container received in said blood collecting chamber; means for evacuating air from said blood collecting chamber to generate a negative pressure in said blood collecting chamber, to thereby form a blood collecting evacuated chamber; blood being collected into said blood container by negative pressure produced in said blood collecting evacuated chamber; weight measuring means including a measuring sensor for generating an output signal y corresponding to a weight w of blood collected in said blood container; and control means for calculating the amount of collected blood in said blood container based on the output signal y of said measuring sensor being in a given relationship with the measured weight w of the collected blood, which is expressed as a function $y = f(w)$, where $f(w)$ comprises at least one constant value (a, b), said control means including memory means for storing specific values of said at least one constant (a, b) of the function $y = f(w)$ of said measuring sensor. Further provided is means for setting said control means in a correction mode, before starting blood collection or after completion of blood collection in said blood container, and wherein in the correction mode, said measuring sensor senses the weight of n samples, where n is an integer of 2 or more, of known weight and said output signal of said measuring sensor is coupled to said control means which calculates the known weight based on said function $y = f(w)$ and corrects said at least one constant value (a, b) of said function $y = f(w)$ if the calculated weight is not the same as said known weight, and said control means automatically rewrites the corrected value of said at least one constant value in said memory means, thus correcting the measuring characteristic of said measuring sensor. The control means thereafter calculates the weight of the collected blood based on said output signal y, said function $y = f(w)$, and said corrected values of said at least one constant value (a, b). Further provided is a pressure measuring means including a pressure sensor for detecting the pressure in the blood collecting evacuated chamber and for generating an output z which is a function of the pressure detected by said pressure sensor. The control means calculates a pressure based on said output z of said pressure sensor being in a given relationship with the measured pressure p, which is expressed as a function $z=f(p)$, where $f(p)$ comprises at least one further constant value (c, d); and said memory means of said control means stores specific values of said at least one further constant value (c, d) of the function $f(p)$ of said pressure sensor. Wherein when said control means is in said correction mode, said pressure sensor senses the pressure of n known pressure amounts, where n is an integer of 2 or more, and said output signal z of said pressure measuring means is coupled to said control means for calculating the known pressure based on said function $z=f(p)$ and correcting said at least one further constant value (c, d) of said function $z=f(p)$ if the calculated pressure is not the same as said known pressure, and said control means automatically rewrites the corrected value of said at least one further constant value in said memory means, thus correcting the measuring characteristic of said pressure sensor.

According to a further feature of the invention, an output y of said measuring sensor is taken out at predetermined intervals when a measured weight w of collected blood is zero, and an off-set value of said function $y=f(w)$ is corrected on the basis of said output taken at said predetermined intervals.

Preferably, the measuring sensor comprises a weight sensor for measuring the weight of collected blood. The at least one constant value of said function $y=f(w)$ preferably comprises two constant values (a and b), and the at least one further constant value of said function $z=f(p)$ preferably comprises two further constant values (c and d).

DETAILED DESCRIPTION

Figure 1:
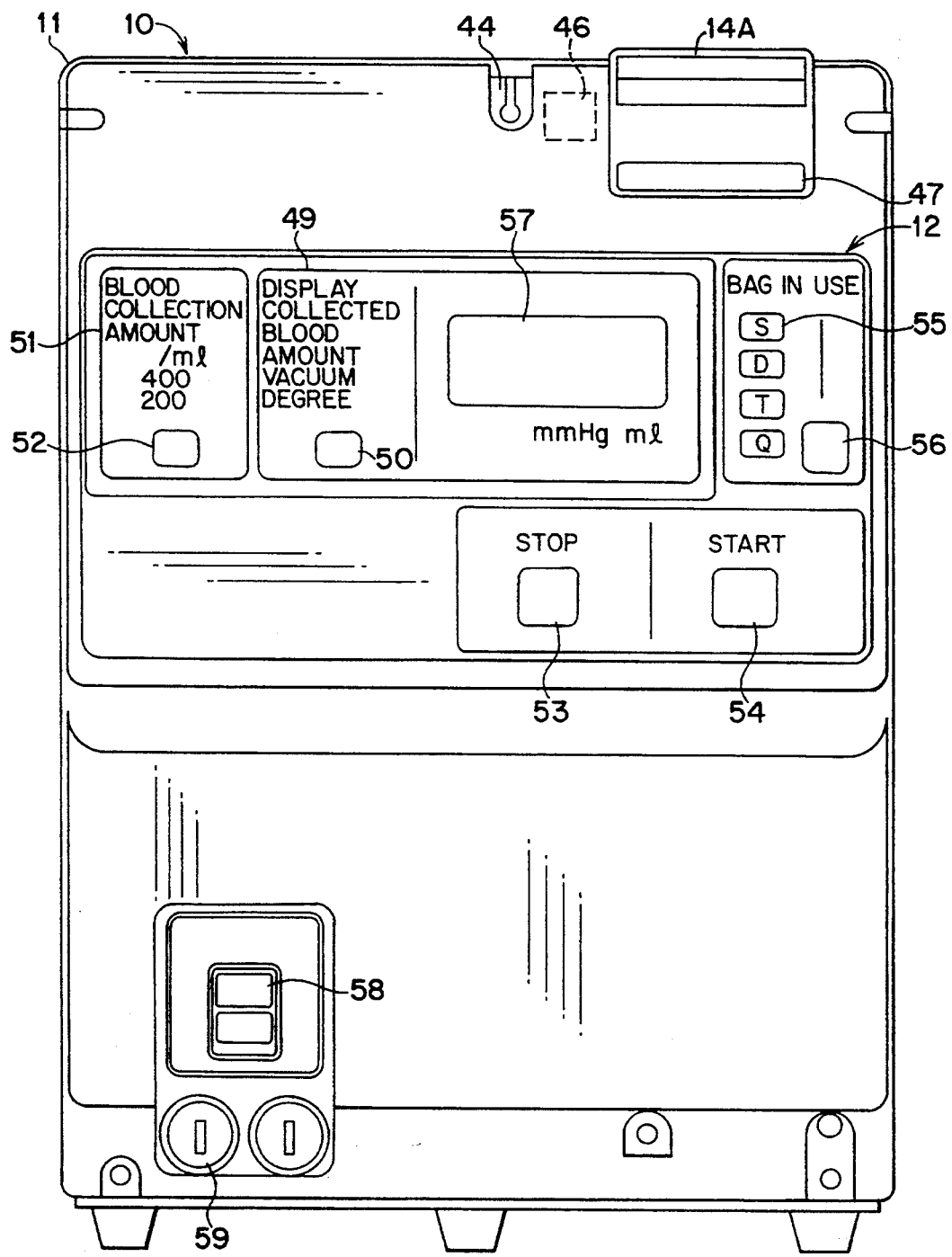
FIG. 1 is a front view showing a blood collecting apparatus in accordance with one embodiment of the present invention.
Figure 2:
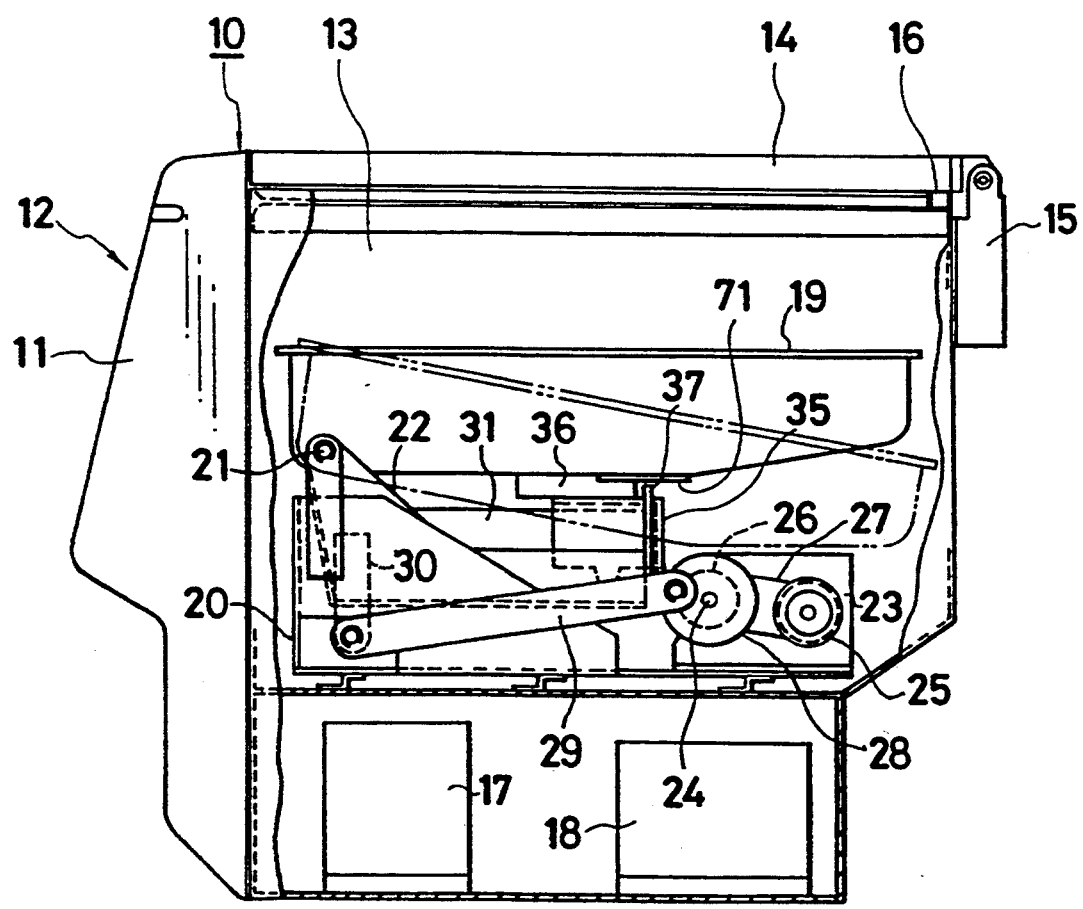
FIG. 2 is a partially cutaway side view showing essential parts of the apparatus shown in FIG. 1.
Figure 3:
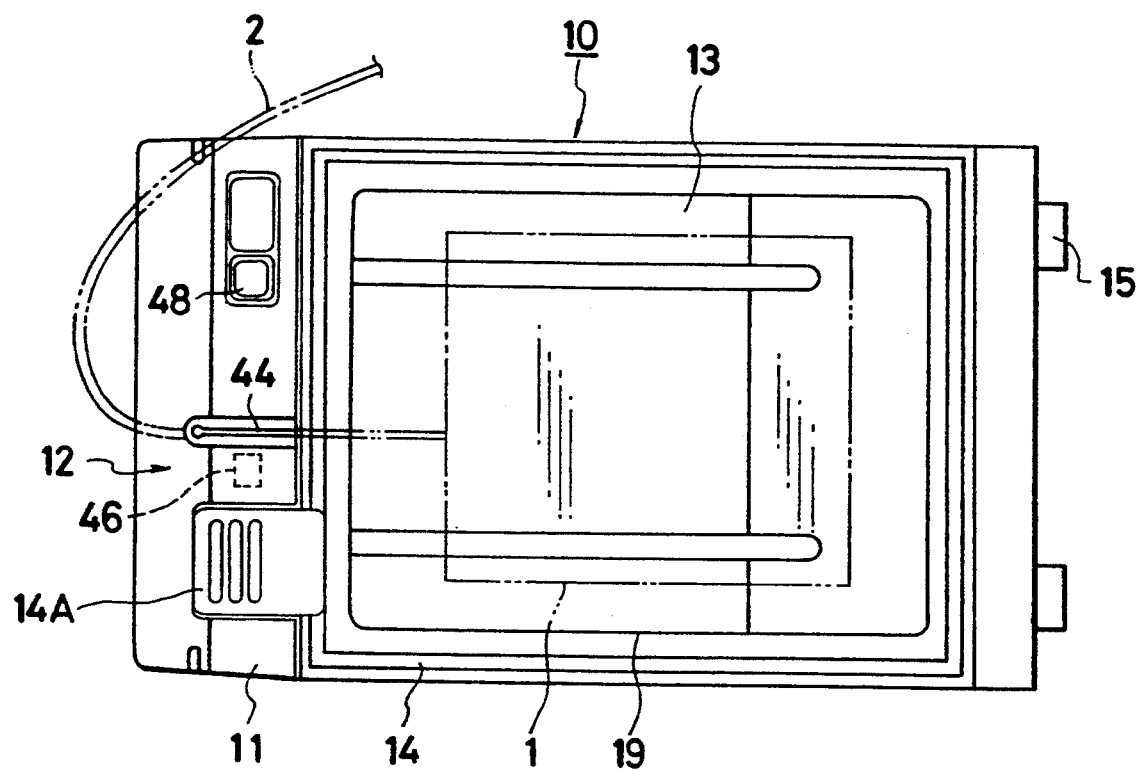
FIG. 3 is a plan view of the apparatus shown in FIG. 1.
Figure 4:
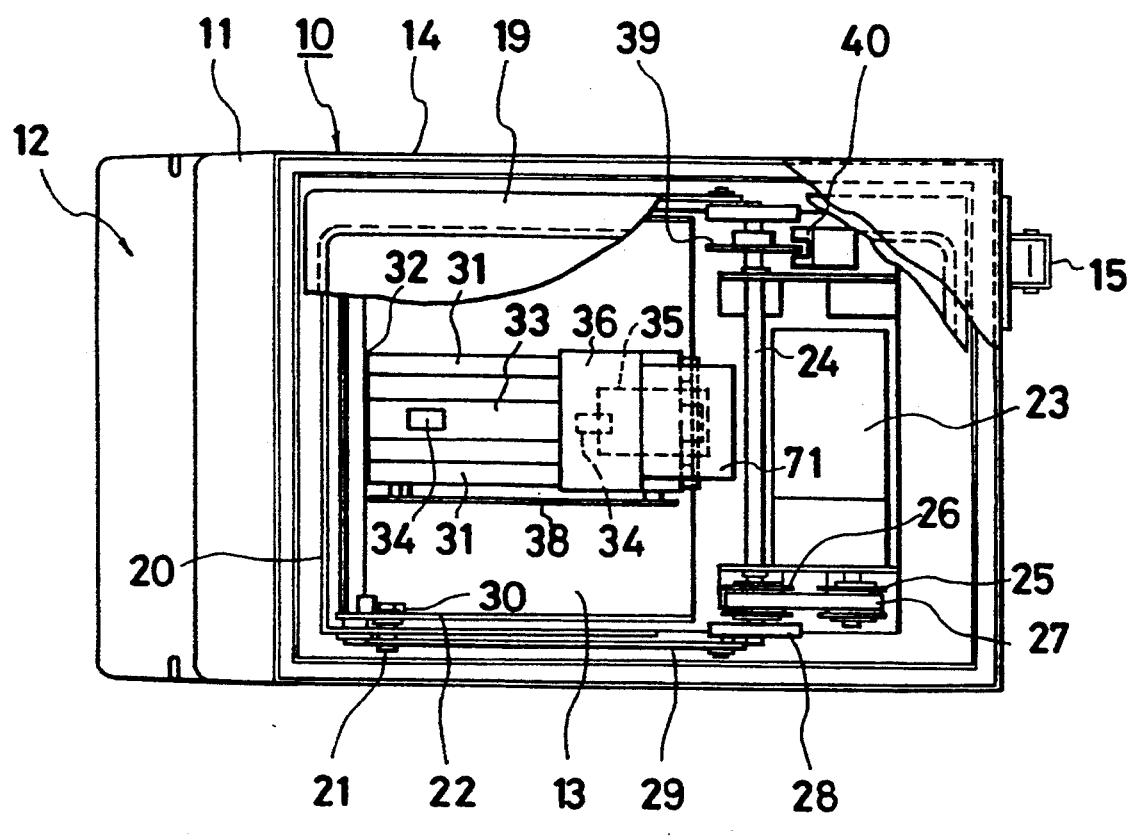
FIG. 4 is a partially cutaway plan view showing essential parts of the apparatus shown in FIG. 1.

As shown in FIGS. 1 to 4, a blood collecting apparatus 10 has a display panel 12 on the front surface of a housing 11, and a blood collecting evacuated chamber 13 formed inside the housing 11. Reference numeral 14 denotes a cover for opening and closing the blood collecting evacuated chamber 13; 15, a hinge for the cover 14; and 16, a sealing rubber for sealing the blood collecting evacuated chamber 13. Reference numeral 14A denotes a handle of the cover 14. The blood collecting apparatus 10 also has a vacuum pump 17 and a control device 18 accommodated within the housing 11 at lower positions thereof.

The blood collecting evacuated chamber 13 of the blood collecting apparatus 10 communicates with a suction port 17A (FIG. 5) of the vacuum pump 17 so as to enable pressure reduction in chamber 13, and the chamber 13 is provided with a bag supporting plate 19 supporting a blood bag (blood container) 1 formed of polyvinyl chloride or the like. The blood collecting apparatus 10 collects blood while the blood collecting evacuated chamber 13 is in its pressure reduced condition, and while a predetermined negative pressure is applied to the blood bag 1 supported by the bag supporting plate 19. During this time, the blood collecting apparatus 10 operates to swing the bag supporting plate 19 intermittently given periods at a predetermined cycle interval so as to agitate blood together with an anticoagulant, such as heparin, already charged in the blood bag 1. The apparatus also operates to measure the amount of collected blood by measuring the weight of the blood bag 1.

The structure within the blood collecting apparatus 10 for swinging the above-described bag supporting plate 19 and the structure for measuring the weight of the blood bag 1 within the blood bag 1 will now be described.

A base 20 is provided on the bottom of the blood collecting evacuated chamber 13. The base 20 supports, through a supporting shaft 21, a swingable frame 22 capable of swinging. A swinging motor 23 is fixed to the base 20, and a drive shaft 24 driven by the swinging motor 23 is supported by the base 20. Reference numerals 25 and 26 denote toothed pulleys, while reference numeral 27 denotes a toothed belt. A crank wheel 28 is fixed to one end of the drive shaft 24. A link 29 is connected, at one end thereof, to a position on the radius of rotation of the crank wheel 28, the other end of the link 29 being connected to a link piece 30 integral with the swingable frame 22.

A pair of weigher mounting blocks 31 are fixed to the upper surface of the swingable frame 22, and a weigher (weight measuring sensor means) 33 is cantilevered by a supporting plate 32 disposed across the end portions of these mounting blocks 31. The weigher 33 is provided with strain gauges 34 which are attached to two positions on the upper surface of the weigher and two positions on the lower surface of the same in such a manner as to form a Wheatstone bridge circuit, and which serve as a weight sensor. The bag supporting plate 19 is fixed to the tip portion of the weigher 33 through a weighing table 35 and a supporting plate 36. Reference numeral 37 denotes a stopper for preventing lateral vibration of the weigher 33, and reference numeral 38 denotes a weight sensor amplification unit.

With the above-described construction, within the blood collecting apparatus 10, the operation of the swinging motor 23 causes the rotation of the drive shaft 24 and the crank wheel 28, whereby the swingable frame 22 is swung, in turn causing the swinging of the bag supporting plate 19 supported by the swingable frame 22 through the weigher 33. Also within the blood collecting apparatus 10, the bag supporting plate 19 is supported by the weigher 33 cantilevered by the swingable frame 22 through the mounting blocks 31 and the supporting plate 32, whereby the weight of the blood bag 1 is measured on the basis of change in the output of the strain gauges 34 in response to the flexural deformation of the weigher 33, so as to measure the amount of collected blood.

The blood collecting apparatus 10 also has the following arrangement. The rotational position of a detection cam 39 provided at the second end of the drive shaft 24 is detected by an optical sensor 40, so as to control the driving of the swinging motor 23. This allows the bag supporting plate 19 to be temporarily stopped at its lowermost descent point (the bottom dead center) and to be held in its state of maintaining a certain attitude, in which condition, the weight of the blood bag 1 is measured in the above described manner.

Figure 5:
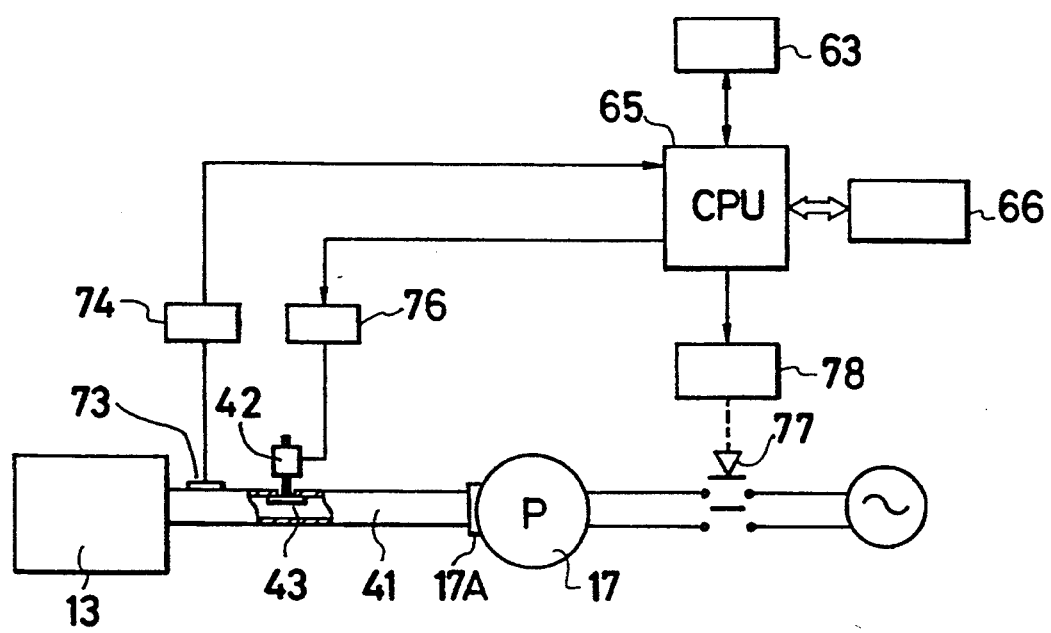
FIG. 5 is a schematic illustration of a vacuum circuit.

As shown in FIG. 5, within the blood collecting apparatus 10, the suction port 17A of the vacuum pump 17 is connected to the blood collecting evacuated chamber 13 via a vacuum pipe 41. A solenoid valve 43 is provided at an intermediate portion of the vacuum pipe 41, which valve closes when an evacuation solenoid 42 is energized, whereas it opens under weight when the evacuation solenoid 42 is deenergized. The blood collecting apparatus 10 performs the on/off control of the vacuum pump 17 so as to form a certain negative pressure (a certain degree of vacuum) within the blood collecting evacuated chamber 13. At the completion of blood collection, the evacuation valve 43 is opened, thereby opening the blood collecting evacuated chamber 13 to the atmosphere.

The blood collecting apparatus 10 further includes a tube holder 44 on a front-side upper portion of the housing 11 which is adjacent to the blood collecting evacuated chamber 13, so as to enable the pulling out a blood collecting tube 2 communicating with the blood bag 1 accommodated in the blood collecting evacuated chamber 13. The tube holder 44 is provided with a tube clamp (blood collection stopping means) 46 driven by a tube clamp solenoid 45. The tube clamp 48 is operable to clamp and press on the blood collecting tube 2 until the tube is closed so as to stop the action of collecting blood into the blood bag 1. Reference numeral 47 denotes a clamp release button for the tube clamp 46, and reference numeral 48 denotes a clamp button for actuating the tube clamp 46 in emergency.

The display panel 12 of the blood collecting apparatus 10 has a lamp 49 for switchingly displaying the collected blood amount/vacuum degree, a collected blood amount/vacuum degree selection switch 50, a lamp 51 for switchingly displaying 400 ml/200 ml, a 400 ml/200 ml selection switch 52, a stop switch 53, a start switch 54, a lamp 55 for displaying the bag in use, a bag-in-use selection switch 56, and a portion 57 for displaying the collected blood amount/vacuum degree. The blood collecting apparatus 10 further includes a power switch 58 and a fuse holder 59 which are at lower portions on the front surface of the housing 11, as well as a power source connector 60 at a lower portion on the reverse surface of the housing 11.

Figure 6:
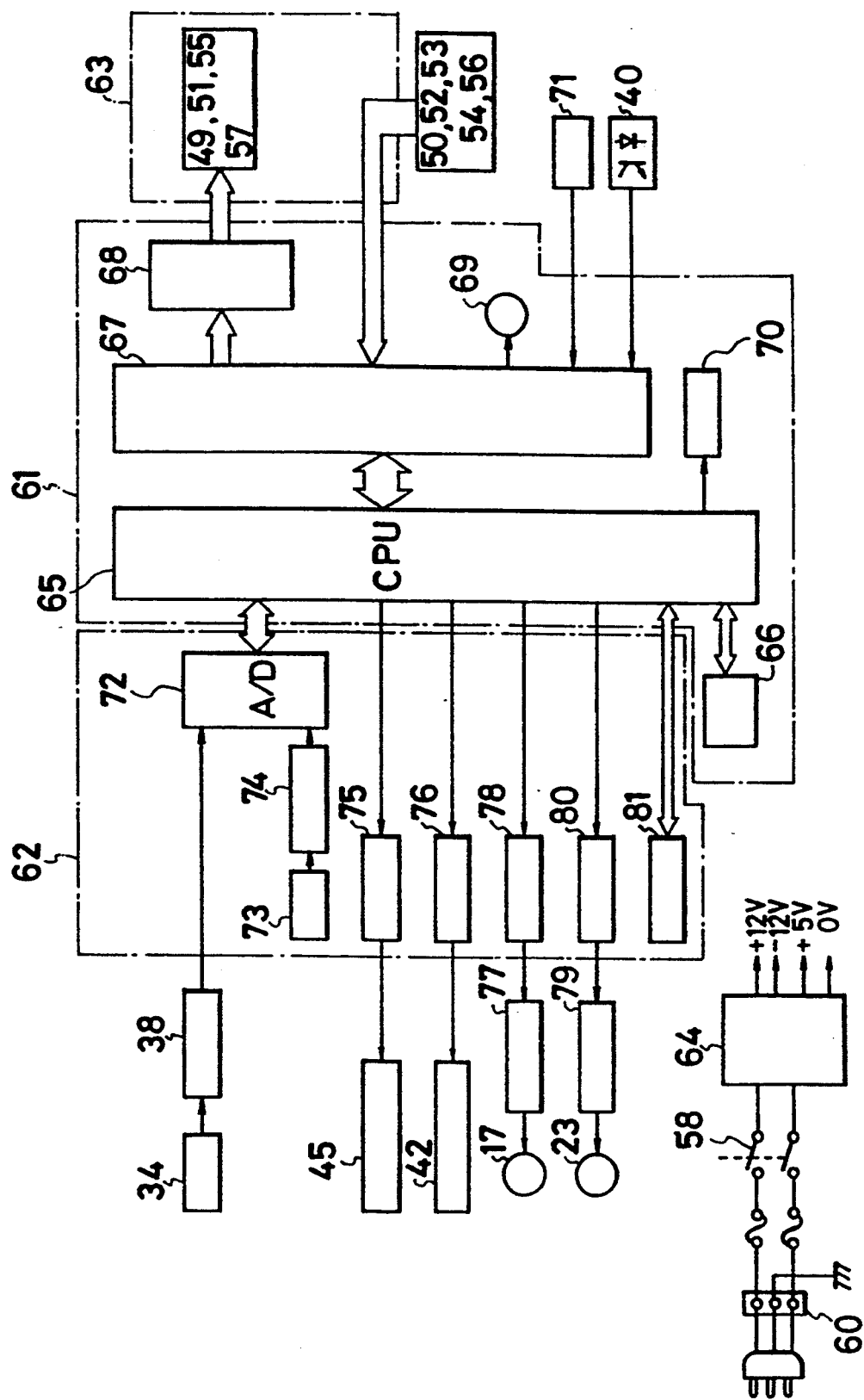
FIG. 6 is a control block diagram.
Figure 7:
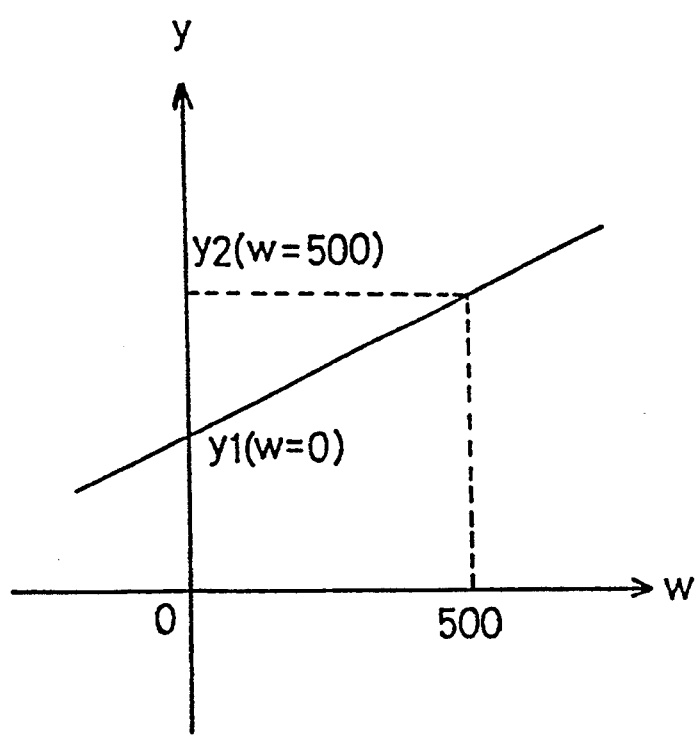
FIG. 7 is a diagram showing a method for determining the characteristic of a sensor.
Figure 8:
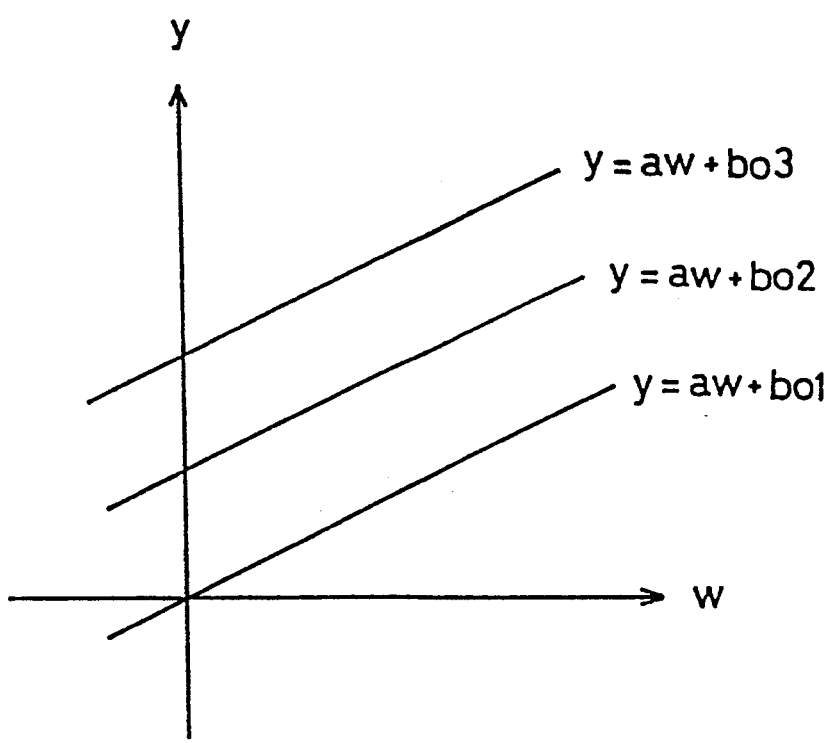
FIG. 8 is a diagram showing a drifted state when the sensor is offset.

Next, a description will be given of the control device 18 of the blood collecting apparatus 10. As shown in FIG. 6, the control device 18 mainly comprises a main control circuit 61, a drive circuit 62, and a display circuit 63. Denoted by 64 is a power source unit.

The main control circuit 61 includes a CPU 65 (central processing unit); including a memory into which a control program for effecting a series of operations of the apparatus 10 is written, a memory (storing means) 66, an input/output control section 67, an LED (light emitting diode) drive circuit 68, a buzzer 69, and a fail-safe circuit 70. Detection signals from the optical sensor 40 for detecting the swinging position of the bag supporting plate 19 and from a blood leakage sensor 71 for detecting leakage of blood from the blood bag 1 are transmitted to the input/output control section 67.

The above-mentioned memory 66 comprises a nonvolatile memory such as an EA-ROM or EEP-ROM, and it allows the rewriting and the reading of stored data, while being capable of holding stored data without any application thereto of power source voltage. The memory 66 stores data such as ① the negative pressure to be generated in the blood collecting evacuated chamber 13, ② the set amount of blood to be collected into the blood bag 1, ③ the reference time during which the vibration of the blood bag 1 is to be stopped at the blood collection terminating stage, and ④ specific constants (a, b, c and d) of sensors as will be described hereinafter.

The buzzer 69 generates sounds in one of different sound-generating manners in accordance with, e.g., ① the completion of blood collection, ② the occurrence of an error in the negative pressure generated in the blood collecting evacuated chamber 13, ③ the occurrence of an error in the rotation of the swinging motor 23, and ④ the detection of blood leakage by the blood leakage sensor 71.

The fail-safe circuit 70 checks the occurrence of runaway of the CPU 65, and, at the time of runaway, stops the apparatus in its safe condition.

The drive circuit 62 is connected to the main control circuit 61, and it has an A/D conversion circuit 72. The weight sensor amplification unit 38, to which the above-described strain gauges 34 are connected, is connected to the A/D conversion circuit 72. A pressure sensor 73 provided in the above-described vacuum pipe 41 in order to detect the negative pressure within the blood collecting evacuated chamber 13 is connected to the A/D conversion circuit 72 via a pressure sensor amplification circuit 74.

With this arrangement, the CPU 65 of the control device 18 calculates the weight of collected blood on the assumption that the output y of the strain gauges 34 is in a certain relationship with the measured weight w of collected blood, which can be expressed as the linear function $y=aw+b$. Also, on the assumption that the output z of the pressure sensor 73 is in a certain relationship with the measured pressure p, which can be expressed as the linear function $z=cp+d$, the CPU 65 calculates the pressure.

The drive circuit 62 also has ① a solenoid drive circuit 75 for controlling the tube clamp solenoid 45, ② a solenoid drive circuit 76 for controlling the evacuation solenoid 42, ③ a pump drive circuit 78 for turning on/off a power supply switch 77 for the vacuum pump 17, and ④ a motor drive circuit 80 for turning on/off a power supply switch 79 for the swinging motor 23.

The CPU 65 of the control device 18 receives the detection output of the pressure sensor 73 and the set pressure within the blood collecting evacuated chamber 13, which is among data stored in the memory 66, and it on/off controls the power supply swich 77 for the vacuum pump 17, as stated before, in such a manner that detected pressure coincides with the set pressure. This operation causes the negative pressure within the blood collecting evacuated chamber 13 to undergo fine changes within a fixed range of the set pressure, so that, as a result, a constant pressure condition is achieved.

Next, a description will be given of the procedure for the blood collecting operation performed by the blood collecting apparatus 10.

① The power switch 58 is turned on.

② The amount of blood to be collected is selected by means of the 400 ml/200 ml selection switch 52. The result of this selection is displayed by the display lamp 51.

④ The bag to be used is selected by means of the bag-in-use selection switch 56. The result of this selection is displayed by the display lamp 55. The bag in use may be one of the following types: the single (S) type solely comprising the main bag, and types further comprising at least one small bag, i.e., the double (D) type, the triple (T) type, and the guadruple (Q) type.

④ A blood collecting needle provided at the tip of the blood collecting tube 2 is stuck into the donor, and this is followed by the collection of blood to a certain extent.

⑤ The blood collecting bag 1 is received in the blood collecting evacuated chamber 13 and is placed on the bag supporting plate 19. The blood collecting tube 2 is set in the tube holder 44. The cover 14 is shut.

⑥ The start switch 54 is turned on. The control device 18 controls the driving of the vacuum pump 17 and the swinging motor 23 in such a manner that blood is collected with pressure reduction in the blood collecting evacuated chamber 13, while the bag supporting plate 19 is swung. The control device 18 also operates, at a timing at which the bag supporting plate 19 temporarily stops at its lowermost descent point, to receive the output of the weight sensor amplification unit 38, detect the measured amount of blood collected in the blood bag 1, and calculate the amount (volume) of blood yet to be collected, by using the set blood collection amount, the specific gravity of blood, and the previously-registered weight of the blood bag 1, these data being written in the memory 66, and using the following equation (1):

Yet-to-be-collected blood amount (ml)=[set blood collection amount (g)+previously-registered weight (g)−collected blood measured amount (g)]/specific gravity (g/ml)     (1)

⑦ The control device 18 causes the tube clamp 46 to clamp and press on the blood collecting tube 2 until the tube is closed so as to stop the action of collecting blood into the blood bag 1 under the condition that the remaining amount of collected blood obtained as a result of the abovementioned calculation has reached zero. At this time, the control device 18 is operated to stop the vacuum pump 17 and to open the exhaust valve 43 to open the blood collecting evacuated chamber 13 to the atmosphere.

⑧ After the completion of the above-described blood collection, the control device 18 causes a re-driving of the swinging motor 23 for a certain time, so as to again swing the bag supporting plate 19. Thereafter, the buzzer sounds to indicate the completion of blood collection.

⑨ The clamp release button 47 is turned on, the cover 14 is opened, the blood collecting tube 2 is removed from the tube holder 44, and the blood collecting bag 1 is taken out of the blood collecting evacuated chamber 13.

FIRST EMBODIMENT

In the CPU 65 of the control device 18, the characteristics of the strain gauges 34 and the characteristic of a pressure sensor 73 are corrected in an early stage and in a transit stage of the use of the blood collecting apparatus 10 through procedures (A) and (B) set forth hereunder.

(A) The output $y_i$ of the strain gauges 34 for two values of the respective known weight $w_i$ of collected blood is uptaken and the constants a and b included in the above-mentioned function $y=aw+b$ are corrected on the basis of such uptaken data. Concretely, this correction is made in accordance with the following procedures ①~⑤.

① The acting mode of the CPU 65 is set to the mode for detecting and correcting the weight by a mode selection switch 81 which the drive circuit 62 is provided with, in the state where the power switch 58 is turned on and the blood collection is not yet started or the blood collection is already completed (the weight of collected blood is zero).

② The CPU 65 stores the output $y_1$ (w=0) of the strain gauges 34 when w=0 as described in ①.

③ The operator puts a known weight of, for instance, w=500 g on the bag supporting plate 19. At this time, the operator sets the display value of the display portion 57 to "500 g" (the display value is reduced by actuation of the stop switch 53 and increased by actuation of the start switch 54), so that the output $y_2$ (w=500) of the strain gauges 34 is entered into the CPU 65 by actuation of the selection switch 50 when w=500 g.

④ The CPU 65 calculates the constants a and b of the linear function $y=aw+b$ from two data $y_1$ (w=0) and $y_2$ (w=500) of the above ② and ③ and writes the results of the calculation into the memory 66. At this time, the buzzer 69 generates sounds.

⑤ Thereafter, the operator puts other known weight of, for example, w=800 g on the bag supporting plate 19. The CPU 65 calculates the weight w at this time using a and b calculated in the above ④ and the output $y_3$ of the strain gauges 34 of this time and displays the result $w_3$ of this calculation on the display portion 57. If the display value at the display portion 57 becomes "800 g", the correction is completed, and if the display value is different from "800 g", the CPU 65 judges that there is something wrong with the sensor itself or the surroundings of the sensor and corrects constants a and b.

(B) The output $z_i$ of the strain gauges 34 for values of a respective known pressure $p_i$ is uptaken and the constants c and d constituting the above-mentioned function $z=cp+d$ are corrected on the basis of such uptaken data. Concretely, this correction is made in accordance with the following procedures ①~⑤.

① The acting mode of the CPU 65 is set to the mode for detecting and correcting the pressure by a mode selection switch 81 which the drive circuit 62 is provided with, in the state where the power switch 58 is turned on and the blood collection is not yet started or the blood collection is already completed (the negative pressure in the blood collecting evacuated chamber 13 is zero).

② The CPU 65 stores the output $z_1=1$ (p=0) when p=0 in the above ①.

③ Then, the CPU 65 automatically actuates the vacuum pump 17 to form a saturated evacuated pressure state in the collecting blood evacuated chamber 13. The operator considers the negative pressure, for example, p=−150 mmHg, in the blood collecting evacuated chamber 13 as already known by a manometer inserted through the blood collecting evacuated chamber 13. The operator sets the display value of the display portion 57 to "−150 mmHg" (the display value is reduced by actuation of the stop switch 53 and increased by actuation of the start switch 54), so that the output $z_2$ ($p=-150$) of the pressure sensor 73 is entered into the CPU 65 by actuation of the selection switch 50 when $p=-150$ mmHg.

④ The CPU 65 calculates the constants c and d of the linear function $z=cp+d$ from two data z1 ($p=0$) and z2 ($p=-150$) of the above ② and ③ and writes the results of the calculation into the memory 66. At this time, the buzzer 69 generates sounds.

⑤ Thereafter, the operator forms a new saturated evacuated pressure in the blood collecting evacuated chamber 13 by releasing pressure from an intermediate portion of the vacuum pipe 41 or by other means and obtains, for example, $p=-100$ mmHg through the manometer as in the above ③. The CPU 65 calculates the pressure p at this time using c and d calculated in the above ④ and the output z3 of the strain gauges 34 at this time and displays the result p3 of this calculation on the display portion 57. If the display value of the display portion 57 becomes "$-100$ mmHg", the correction is completed, and if the display value is different from "$-100$ mmHg", the CPU 65 judges that the sensor itself or the surroundings of the sensor are something wrong and corrects the same.

Next, operation of the above-mentioned embodiment will be described.

According to the above-mentioned embodiment, the constants a and b of the function $y=aw+b$ expressing that the output y of the strain gauges 34 is in a certain relationship with the measured weight w of collected blood can be corrected through the procedure stated in the above-mentioned procedure (A). That is, the characteristic of the sensor for measuring the amount of collected blood can be corrected with ease and the accuracy in measurement of the amount of collected blood can be obtained without requiring a conversion circuit.

The constants c and d of the function $z=cp+d$ expressing that the output z of the pressure sensor 79 is in a certain relationship with the negative pressure p of the blood collecting evacuated chamber 13 can also be corrected through the procedures stated in the above procedure (B). That is, the characteristic of the pressure sensor can also be corrected with ease and the accuracy in measurement of pressure generated within the blood collecting evacuated chamber can also be obtained without requiring a conversion circuit.

In the above-mentioned embodiment, in step ③ of the above procedure (A) and in step ③ of the above procedure (B), when the operator makes the known weight wi of collected blood and the known pressure pi entry into the CPU 65, the entry values are displayed on the display portion 57. Accordingly, operation of the operator and the entry values into the CPU 65 can visually be recognized.

SECOND EMBODIMENT

In the CPU 65 of the control device 18, the offset value b of the strain gauges 34 and the offset value d of the pressure sensor 73 are corrected in the state where the power switch 58 is turned on and the blood collection is not yet started or the blood collection is already completed (the weight of collected blood is zero and the negative pressure in the blood collecting evacuated chamber 13 is also zero) through the procedures (A) and (B) set forth hereunder.

(A) The CPU 65, as mentioned above, automatically uptakes the output y0 of the strain gauges 34 at predetermined cycle in the state where the measured weight w of collected blood is zero and corrects b of the above-mentioned function $y=aw+b$ on the basis of such uptaken y0. Concretely, with reference to the offset value b01 which was already written into the memory 66 in the preceding correction stage, if the above-mentioned y0, which is in the correction stage at this time, satisfies the expression ① $y0 \leq b01+m$ (for example, $m=3$ g), the CPU 65 adopts the above-mentioned y0 as a new offset value and stores the new offset value in the memory thereof, and if it satisfies the expression ② $y0>b01+m$, the CPU 65 judges that a substance is loaded on the sensor and adopts b01 at the preceding time also for this time.

(B) The CPU 55, as mentioned above, automatically uptakes the output z0 of the pressure sensor 73 at predetermined intervals in the state where the negative pressure p in the blood collecting evacuated chamber 13 is zero and corrects the above-mentioned function $z=cp+d$ on the basis of such uptaken z0. Concretely, with reference to the offset value d01 which was already written into the memory 66 in the preceding correction stage, if the above-mentioned z0, which is in the correction stage at this time, satisfies the expression ① $z0 \leq d01+r$ (for example, $r=3$ mmHg), the CPU 65 adopts the above-mentioned z0 as a new offset value and stores the new offset value in the memory thereof, and if it satisfies the expression ② $z0>d01+r$, the CPU 55 judges that pressure changes have already taken place owing to a start of blood correction and maintains d01 to the preceding time also for this time.

Next, operation of the above-mentioned embodiment will be described.

According to the above-mentioned second embodiment, the offset value b of the function $y=aw+b$ expressing that the output y of the strain gauges 34 is in a certain relationship with the measured weight w of collected blood can automatically be corrected at predetermined intervals through the above-mentioned procedure (A). Accordingly, the change of the offset value b in the output of the strain gauges 34 caused by drift can normally and automatically be corrected and the accuracy in measurement of the weight of collected blood can be obtained.

Similarly, the offset value d of the function $z=cp+d$ expressing that the output z of the pressure sensor 73 is in a certain relationship with the measured pressure p is also automatically corrected at predetermined intervals through the above-mentioned procedure (B). Accordingly, the changes of the offset value d of the output of the pressure sensor 73 caused by drift can also normally and automatically be corrected and the accuracy in measurement of the pressure to be generated in the blood collecting evacuated chamber 13 can also be obtained.

According to the present invention, the characteristic of the sensor for measuring the amount of collected blood can be corrected with ease and the accuracy in measurement of the amount of collected blood can be obtained.

According to the present invention, the characteristic of the pressure sensor can also be corrected with ease and good accuracy in measurement of the pressure to be generated in the blood collecting evacuated chamber can also be obtained.

According to the present invention, the changes of the offset value of the output of the sensor for measuring the amount of collected blood caused by drift can normally and automatically be corrected, and good accuracy in measurement of the amount of collected blood can be obtained.

According to the present invention, the changes of the offset value of the output of the pressure sensor caused by drift can also normally and automatically be corrected, and good accuracy in measurement of the pressure to be generated in the blood collecting evacuated chamber can also be obtained.

The present invention is basically likewise applicable even if the above-mentioned functions $y=f(w)$ and $z=f(p)$ are not linear functions but quadric functions, index functions and logarithms.

We claim:

1. A blood collecting apparatus (10), comprising:
  a blood collecting chamber (13);
  a blood container (1) received in said blood collecting chamber (13);
  means for evacuating air from said blood collecting chamber (13) to generate a negative pressure in said blood collecting chamber (13), to thereby form a blood collecting evacuated chamber (13);
  weight measuring means including a weight measuring sensor (33) for generating an output signal y corresponding to a weight w of blood collected in said blood container (1);
  control means (65) for calculating the amount of collected blood in said blood container (1) based on the output signal y of said weight measuring sensor (33) being in a given relationship with the measured weight w of the collected blood, which is expressed as a function $y=f(w)$, where f(w) comprises at least one constant value (a, b),
  said control means (65) including memory means (66) for storing specific values of said at least one constant (a, b) of the function $y=f(w)$ of said weight measuring sensor (33);
  means for setting said control means (65) in a correction mode, before starting blood collection or after completion of blood collection in said blood container, and wherein in the correction mode, said weight measuring sensor (33) senses the weight of n samples, where n is an integer of 2 or more, of known weight and said output signal of said weight measuring sensor is coupled to said control means which calculates the known weight based on said function $y=f(w)$ and corrects said at least one constant value (a, b) of said function $y=f(w)$ if the calculated weight is not the same as said known weight, and said control means automatically rewrites the corrected value of said at least one constant value in said memory means (66), thus correcting the measuring characteristic of said weight measuring sensor (33);
  said control means (65) thereafter calculating the weight, of the collected blood based on said output signal y, said function $y=f(w)$, and said corrected values of said at least one constant value (a, b);
  means for taking out an output signal y of said weight measuring sensor (33) at predetermined intervals when a measured weight w of collected blood is zero, and wherein an off-set value of said function $y=f(w)$ is corrected on the basis of said output signal y taken out of said weight measuring sensor (33) at said predetermined intervals;
  a pressure measuring means including a pressure measuring sensor (73) for detecting the pressure in the blood collecting evacuated chamber (13) and for generating an output z which is a function of the pressure detected by said pressure measuring sensor;
  said control means (65) calculating a pressure based on said output z of said pressure measuring sensor (73) being in a given relationship with the measured pressure p, which is expressed as a function $z=f(p)$, where f(p) comprises at least one further constant value (c, d);
  said memory means (66) of said control means (65) storing specific values of said at least one further constant value (c, d) of the function f(p) of said pressure measuring sensor (73); and
  wherein when said control means is in said correction mode, said pressure measuring sensor (73) senses the pressure of n known pressure amounts, where n is an integer of 2 or more, and said output signal z of said pressure measuring means is coupled to said control means (65) for calculating the known pressure based on said function $z=f(p)$ and correcting said at least one further constant value (c, d) of said function $z=f(p)$ if the calculated pressure is not the same as said known pressure, and said control means automatically rewrites the corrected value of said at least one further constant value in said memory means (66), thus correcting the measuring characteristic of said pressure measuring sensor.

2. The blood collecting apparatus of claim 1, wherein said at least one constant value of said function $y=f(w)$ comprises two constant values (a and b).

3. The blood collecting apparatus of claim 2, wherein said at least one further constant value of said function $z=f(p)$ comprises two further constant values (c and d).

4. The blood collecting apparatus of claim 1, wherein said at least one further constant value of said function $z=f(p)$ comprises two further constant values (c and d).

* * * * *